United States Patent [19]

Nowinski et al.

[11] Patent Number: 4,511,478
[45] Date of Patent: Apr. 16, 1985

[54] POLYMERIZABLE COMPOUNDS AND METHODS FOR PREPARING SYNTHETIC POLYMERS THAT INTEGRALLY CONTAIN POLYPEPTIDES

[75] Inventors: Robert C. Nowinski; Allan S. Hoffman, both of King County, Wash.

[73] Assignee: Genetic Systems Corporation, Seattle, Wash.

[21] Appl. No.: 550,929

[22] Filed: Nov. 10, 1983

[51] Int. Cl.³ .................. C08L 89/00; C08H 1/00
[52] U.S. Cl. .................. 210/691; 526/238.1; 525/54.1; 260/112 R; 260/112 B; 260/112 G; 436/531; 436/535; 436/536; 436/541; 436/543; 436/827; 210/692
[58] Field of Search .................. 525/54.1, 54.11; 526/238.1; 260/112 R, 112 B, 112 G, 112 T, 112.5 R; 210/692, 691; 436/518, 531, 535, 536, 541, 543, 817, 819, 827

[56] References Cited

U.S. PATENT DOCUMENTS 2,853,457  9/1958  Gates, Jr. et al. ............ 526/238.1
3,969,287  7/1976  Jaworek et al. ............ 526/238.1
4,061,466 12/1977  Sjohölm et al. ............ 436/535
4,195,129  3/1980  Fukui et al. ............ 435/182

Primary Examiner—John Kight
Assistant Examiner—Nathan M. Nutter
Attorney, Agent, or Firm—Seed and Berry

[57] ABSTRACT

A method is disclosed for the de novo synthesis of polypeptide-containing polymers. This disclosure also includes a description of, and a method for the preparation of, a class of polymerizable compounds used in the synthesis of polypeptide-containing polymers. These polymerizable compounds are chemical conjugates prepared by covalent linkage of polymerizable organic monomers with specific polypeptides. Soluble monomer/polypeptide conjugates can be polymerized in solution with additional nonderivatized organic monomers to form desired polypeptide-containing polymers. The amount and composition of monomer and monomer/polypeptide conjugates can be varied in order to provide control of (a) molecular spacing, steric accessibility, and number of polypeptide molecules that are integrally incorporated into the polymer backbone, and (b) the chemical and physical structure of the polymer itself. This enables the specific tailoring of polypeptide-containing polymers for particular end-use applications.

5 Claims, 3 Drawing Figures

POLYMERIZABLE COMPOUNDS AND METHODS FOR PREPARING SYNTHETIC POLYMERS THAT INTEGRALLY CONTAIN POLYPEPTIDES

DESCRIPTION

1. Technical Field

The present invention relates to compounds and methods used for the de novo synthesis of organic polymers that contain polypeptides as an integral part of their backbone structure.

2. Background Art

A reaction fundamental to polymer chemistry is the initiation of end-to-end covalent linkages between soluble organic monomeric compounds (monomers) leading to the formation of larger polymeric molecular structures (polymers). Synthetic polymers may be formed from a single monomeric species (homopolymers) or from a mixture of different monomers (copolymers). Linear, branched, or cross-linked structures are possible. By varying the chemical composition or ratios of the monomers, it is possible to form either soluble or insoluble polymers which comprise a broad range of chemical and physical structures. For example, water-soluble monomers (such as acrylamide) may be homopolymerized to form water-soluble homopolymers. They may also be copolymerized with less water-soluble monomers (such as N-alkyl or N,N-dialkyl acrylamides) or with cross-linking monomers (such as N,N'-methylenebisacrylamide) to form water-insoluble copolymer structures. Some water-soluble monomers (such as hydroxyethyl methacrylate or acrylonitrile) may be homopolymerized to form water-insoluble homopolymers.

In the fields of biochemistry and immunology, water-insoluble polymers (such as polyvinyls, polyacrylamides, or polydextrans) have been commonly used as solid-phase supports with passively adsorbed, physically entrapped, or covalently linked proteins in affinity chromatography, enzyme immobilization, and immunoassays. To date, the documented covalent coupling of a polypeptide to a polymer has occurred under circumstances in which the polypeptide was provided in soluble form and the polymer was provided as a preformed soluble or insoluble polymer material.

For purposes of affinity chromatography (Affinity Chromatography and Related Techniques, Proceedings of the Fourth International Symposium, Veldhoven, The Netherlands, June 22–26, 1981, eds. T. C. J. Gribnau, J. Visser, and R. C. F. Nivard, Elsevier Scientific Publishing Co., N.Y., 1982), antibodies can be covalently bonded to cyanogen bromide-activated beads of Sepharose ® 4B (Pharmacia Fine Chemicals AB, Uppsala, Sweden) or beads of cross-linked acrylic polymers (U.S. Pat. No. 3,957,741). The immobilized antibodies can then be used to specifically bind antigens to the solid surface followed by extensive washing to remove other adsorbed substances. Subsequently, the bound antigens can be eluted from the antibody/polymer matrix by treatment with chaotropic agents, high salt, or low pH buffers. Antibodies have also been confined within capsule membranes for use in affinity chromatography (U.S. Pat. No. 4,257,884).

In certain chemical processes, immobilizing enzymes on insoluble matrices provides a convenient method of selectively controlling a chemical reaction. For example, enzymes entrapped within, or bound to the surface of, polymer beads can be added to reactants in solution for a discrete period of time and then selectively removed by physical procedures, such as centrifugation. Alternatively, chemical reactants in solution may be brought into controlled physical contact with enzymes by chromatography through columns comprised of polymer beads to which enzymes have been covalently coupled. For example, see U.S. Pat. No. 4,195,129. Graft copolymerization has also been employed as a means of enzyme immobilization. For example, D'Anguiro et al. (Biotechnol. Bioeng., vol. 22:2251, 1980) describe graft copolymerizing vinylated enzymes to a preformed polymeric surface.

In immunoassays (see Campbell, D. H. and Weliky, N., Methods in Immunology and Immunochemistry, Editors: Williams and Chase, Vol. 1, Academic Press, N.Y., 1967), antibodies or antigens have been passively adsorbed to plastic surfaces, e.g., the wells of microtiter plates or plastic beads (U.S. Pat. No. 4,225,784) or to latex particles. The solid-phase antibody/polymer matrix provides a selective binding surface which, following an appropriate reaction, can be washed to separate bound from unbound reactants. Alternative uses include (a) the covalent binding of antigens or antibodies to latex beads (U.S. Pat. No. 4,181,636) or high refractive index particles (U.S. Pat. No. 4,401,765) to measure agglutination reactions, or (b) the binding of antibodies to fluorescent polymer beads to provide specific tags for cell surface antigens (U.S. Pat. No. 4,166,105).

While these insoluble polymers are of utility in providing a surface upon which selective biochemical or immunological reactions can occur, the polymers are of limited value in that the spacing, steric accessibility, and number of protein molecules bound per unit length of polymer cannot be precisely or reproducibly controlled. Lot-to-lot variation is commonly encountered during the manufacture of such solid-phase polypeptide/polymer matrices. In certain end-use applications where reproducibility and standarization are essential (e.g., immunoassays), this variation in composition of the solid-phase polymer/polypeptide matrices presents a critical problem. Consequently, there is a need in the art for a method to specifically tailor or molecularly engineer polymer compounds incorporating controlled quantities of polypeptides.

DISCLOSURE OF THE INVENTION

Briefly stated, the invention discloses a method for preparing synthetic polymers which integrally contain specific polypeptides as part of their structure. Essential features of this method include (a) the covalent linkage of soluble organic monomers to selected polypeptides to form soluble monomer/polypeptide conjugates, followed by (b) the copolymerization of these conjugates with nonderivatized monomers to form synthetic copolymers that integrally contain polypeptides in their structure. Utilizing controlled chemical synthesis, comparable to that conventionally practiced in the polymer chemistry field, it is possible to control the spacing, steric accessibility, and number of polypeptide molecules along the backbone of the polymer, providing unique advantages for certain end-use applications.

Accordingly, the present invention is directed to (1) monomer/polypeptide conjugates used in making synthetic polymers that integrally contain one or more polypeptides, (2) methods of making the monomer/polypeptide conjugates, (3) methods of making polymers that incorporate one or more polypeptides, and (4) a method of selectively removing substances from solutions and mixtures by the binding of a monomer/polypeptide conjugate to the substance, and the subsequent polymerization of the conjugate.

A principal advantage of the monomer/polypeptide conjugate is its ability to be incorporated into synthetic polymers under controlled chemical conditions to yield polypeptide-containing polymers with specified compositions and structures. Utilizing methods commonly employed in polymer chemistry, these polypeptide-containing polymers may be engineered to have specific molecular weights, densities, solubilities, physical structures, and polypeptide concentrations. The polypeptide-containing polymers may be formulated to make fibers, particles, beads, films, coatings, gels, tubes, filters, shaped objects, and porous solids, all integrally containing polypeptides.

The monomer/polypeptide conjugates, and their corresponding polypeptide-containing polymers, have utility in immunoassay systems, affinity chromatography, enzyme immobilization, and in the isolation, purification, and/or removal from solution of chemical or biochemical substances which have the capacity to bind to the polypeptide. These procedures can be performed with insoluble polypeptide containing polymers, or alternatively with soluble monomer/polypeptide conjugates which are subsequently polymerized. In the first case, the insoluble polymers provide a solid surface upon which specific binding reactions can occur; with subsequent washing of the solid surface, those substances that bind specifically to the polypeptides incorporated in the polymer can be either purified and/or measured. In the second case, the soluble monomer/polypeptide conjugates can bind to biological substances via specific interactions that are associated with the biological activity of the specified polypeptide (e.g., antibody/antigen reactions). Subsequent initiation of polymerization will result in the formation of soluble or insoluble copolymers with integrally contained polypeptides and their associated biological substances along the polymer backbone. In the case where the resultant polymer is insoluble, this provides a convenient one-step method of separating bound from nonbound substances in a mixture.

Synthetic polymers integrally containing polypeptides would also be expected to have potential biological or chemical activities. For example, polymers integrally containing polypeptides could be used for immunization. Indeed, with chemically synthesized polypeptides corresponding in structure to antigenic determinants, it should be possible to prepare defined polymers that can be utilized as vaccines. Alternatively, synthetic polymers integrally containing natural polypeptides could provide biocompatible and biofunctional surfaces that are useful in in vivo implants or for the extracorporeal treatment of blood.

BEST MODE FOR CARRYING OUT THE INVENTION

Figure 1:
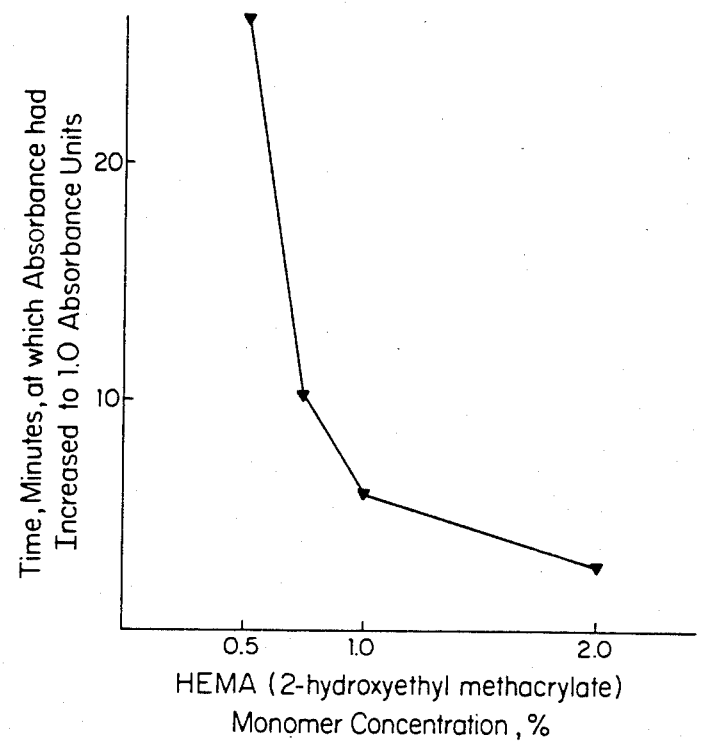
FIG. 1 depicts the effect of monomer (HEMA) concentration on the rate of formation of insoluble HEMA homopolymer particles.

The polymerizable compound of this invention is produced by covalently linking an appropriate monomer with a specific polypeptide. For purposes of the present invention as claimed herein, the term "polypeptide" is defined as including any amino acid, peptide, or polypeptide. The monomer/polypeptide conjugate may then be homopolymerized or copolymerized with additional nonderivatized organic monomer to form polymers integrally containing polypeptides and having the desired properties. For purposes of this disclosure, the phrase "integrally containing" means that the polypeptide is covalently bonded to the polymer backbone as it is formed, rather than being coupled to a preformed polymer.

The polypeptides which may be used include naturally occurring or genetically engineered antibodies, enzymes, antigens, receptors, haptens, lectins, hormones, transport proteins, polypeptide antibiotics, polypeptide drugs, and chemically synthesized peptides and polypeptides which may functionally correspond to any of these listed categories.

Biocompatible monomers which can be used include ethylenically or acetylenically unsaturated monomers containing at least one reactive site for binding to the polypeptide. These reactive sites may include, for example, covalently bondable functionalities, such as hydroxyl, primary amine, carboxyl or sulfhydryl on either the polypeptide or, in the case of glycoproteins, the attached carbohydrate. Monomers may be selected from compounds having the formula:

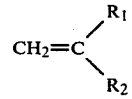

where $R_1$ is H or a lower alkyl radical having from 1 to 8 carbon atoms, and $R_2$ may be:

—COCl
—COOH
—CO$_2$C$_n$H$_{2n}$OH  n=2,3,4
—CH$_2$NH$_2$
—CH$_2$Cl
—CO$_2$C$_2$H$_4$NH$_2$

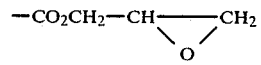

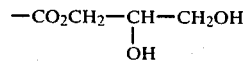

—CHO

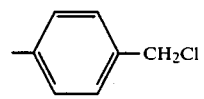

—CO$_2$(CH$_2$)$_2$NCO

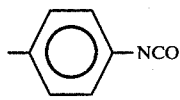

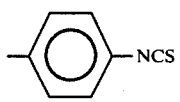

Specific monomers which can be used include acrylic acid, methacrylic acid, acryloyl chloride, methacryloyl chloride, glycidyl acrylate or methacrylate, glycerol acrylate or methacrylate, allylamine, allyl chloride, hydroxy-lower-alkyl-acrylates, such as 2-hydroxyethyl methacrylate or 3-hydroxypropyl methacrylate, and amino-lower-alkyl-acrylates, such as 2-aminoethyl methacrylate. Preferred are monomers which are soluble in water or water/polar organic solvent mixtures.

Covalent bonding of the monomer to the polypeptide or its attached carbohydrate (in the case of glycoproteins) can be carried out by any number of known chemical methods. For example, the monomer and/or the polypeptide can be activated to produce a stable but reactive intermediate which can be subsequently reacted. The polypeptide may also be activated, i.e., by periodate oxidation of the attached carbohydrates, if the polypeptide is a glycoprotein. This reaction forms aldehydes which can then condense with amino groups on the monomers, such as 2-aminoethyl methacrylate, to form a Schiff base. This Schiff base can be reduced with sodium cyanoborohydride to form a stable covalent linkage. The monomer in the form of an acid halide or anhydride may also be directly reacted with the polypeptide in the presence of an acid scavenger to remove acid as it is formed during the reaction. Specifically, bifunctional or hetero-bifunctional reagents may be used. Such bifunctional or hetero-bifunctional reagents are known and can be obtained, for example, from Pierce Chemical Company, Rockford, Ill. The bifunctional and/or hetero-bifunctional reagents may be biodegradable, permitting release of the polypeptide over an extended period of time. In almost all cases, the reaction conditions, i.e., time, temperature, solvent, and pH, should be such as to avoid denaturation and/or degradation of the polypeptide.

Homopolymerization of the monomer/polypeptide conjugate with itself or copolymerization with nonderivatized monomers is initiated by generation of free radicals. Nonderivatized monomers which may used include, for example, ethylenically and/or acetylenically unsaturated monomers, as previously discussed, alkyl acrylates or methacrylates where the alkyl radical contains from 1 to 8 carbons, acrylonitrile and vinyl acetate. Also, cross-linking compounds may be copolymerized with the monomer/polypeptide conjugate. Such cross-linking compounds may include, for example, N,N'-methylenebisacrylamide, or a di-, tri- or tetramethacrylate or acrylate. The relative amounts of the conjugated monomer and nonderivatized monomer employed, the monomer composition and concentration, temperature, solvent, pH, and the particular initiator system utilized allow the specific molecular engineering of a polypeptide-containing polymer. The percentage of derivatized and nonderivatized monomer may vary from traces up to 100%, but the preferable range is between 0.001 to 100% derivatized monomer and 0 to 99.999% nonderivatized monomer.

Polymerization is generally conducted at about room temperature with or without agitation. A surface active agent may or may not be present. Although the reaction may be carried out in the presence of oxygen, it is generally preferred to conduct the reaction in the absence of oxygen or in the presence of a controlled amount of oxygen. The pH range may vary widely from pH 3 to pH 10, although it is preferable to select a pH where the polypeptide remains the most stable, which is typically between pH 6 and pH 8. If a surface active agent is used, suitable compounds, such as sodium dodecyl sulfate, sodium stearate, or nonionic materials, such as polyethylene oxide lauryl ether, may be employed.

The free radicals may be generated by oxidation-reduction initiation, photochemical initiation, ionizing radiation or thermal initiation. An advantage of both oxidation-reduction initiation and photochemical initiation is production of free radicals at reasonable rates at relatively low temperatures, such as ambient or body temperature. Types of oxidation-reduction initiators which may be used include (1) peroxides in combination with a reducing agent, e.g., hydrogen peroxide with ferrous ion, or benzoyl peroxide with an N,N-dialkylaniline or toluidine, and (2) persulfates in combination with a reducing agent, such as sodium metabisulfite or sodium thiosulfate. Specifically, ammonium persulfate, benzoyl peroxide, lauryl peroxide, t-butyl hydroperoxide, t-butyl perbenzoate, cumene hydroperoxide, or mixtures thereof with reducing agents, such as sodium bisulfite or sodium thiosulfate, may be used. It also appears that sodium bisulfite alone may be used for polymerization.

Photoinitiated polymerization may also be used by employing a photoinitiator, such as azodiisobutyronitrile or azodiisobutyroamide, benzoin methyl ether, riboflavin, thiazine dyes, such as methylene blue or eosin, and transition metals, such as ferric chloride or diazidotetramminecobalt (III) azide, in combination with ultraviolet and/or visible light irradiation of the reaction system.

Ionizing radiation may also be employed utilizing radiation from a radioactive source or a particle accelerator.

Polymerization may be carried out in the presence of various physiological materials, such as proteins, and under various physiological conditions, such as neutral pH in isotonic buffered saline solution.

Examples presented here utilize a representative monomer (2-hydroxyethyl methacrylate, HEMA) and a representative polypeptide (mouse monoclonal antibody 2H1, MAb, which reacts with the kappa chain of human IgG). To summarize the examples which follow, Example I demonstrates the polymerization of HEMA monomer in a buffered saline solution. In order to assure noninterference in this polymerization process by "bystander" polypeptides, this reaction was also conducted in the presence of a mixture of normal serum proteins. Example II demonstrates a method of producing an activated form of an acrylic acid monomer which is to be conjugated to the MAb polypeptide. Example III demonstrates the covalent conjugation of the activated acrylic acid monomer to the MAb polypeptide to form the monomer/polypeptide conjugate. To monitor the amount of acrylic acid monomer covalently bound to the MAb polypeptide, the amount of free acrylic monomer in solution before and after the conjugation reaction was determined. Gel separation by isoelectric focusing of MAb heavy and light chains also demonstrated binding of the acrylic monomer to the polypeptide. Example IV demonstrates copolymerization of the monomer/polypeptide conjugate (MAb-M) with additional nonderivatized HEMA monomer, resulting in synthetic polymer particles that integrally contain MAb polypeptides in their structure. For the purpose of demonstration, the MAb-M conjugate was first fluorescence-tagged with fluorescein isothiocyanate. Polymer particles containing these fluorescein-tagged MAb-M polypeptides were then visualized under the fluorescence microscope. Additionally, the fluorescence of individual polymer particles was quantitated by flow analysis using a fluorescence-activated cell sorter.

EXAMPLE I

Polymerization of Hema Monomer in a Buffered Saline Solution

Polymerization of 2-hydroxyethyl methacrylate in the presence of physiological compounds was carried out as follows: to 2.73 mL of distilled water or phosphate-buffered saline, pH 7.4, was added 0.06 to 0.24 mL of 25% (v/v) 2-hydroxyethyl methacrylate (HEMA, Aldrich Chemical Company). Water was added to a final volume of 2.97 mL, as necessary. After bubbling prepurified nitrogen through a Pasteur pipette into the bottom of the cuvet for at least five minutes, 30 microliters of 1M $Na_2S_2O_5$ was added and the precipitation of the resulting polymer was followed at 550 nm with a Beckman Model 26 spectrophotometer. FIG. 1 illustrates the dependence of the rate of precipitation on the concentration of monomer. From this data, a concentration of 2% was chosen.

Inclusion of fetal calf serum, up to 10% (v/v), or "Nonidet P-40", a nonionic detergent, at concentrations up to 1% (w/v), had no effect on the rate of formation of the polymer particles. Since fetal calf serum contains a variety of proteins and other physiological compounds, this indicates that most proteins and physiological compounds will not inhibit formation of the polymer particles. Since nonionic detergents are commonly used in immunoassays to solubilize biological substances, this indicates that it will be possible to utilize detergents in polymerization/immunoassays without interference.

EXAMPLE II

Synthesis of an Activated Acrylic Acid Monomer for Coupling to Antibody

A mixture containing N-hydroxysuccinimide (NHS) (4.6 g, 40 mmol) and acrylol chloride (18 mL, 220 mmol) was refluxed with vigorous stirring for 3 hours in an anhydrous atmosphere and the reaction mixture, a homogeneous solution, was evaporated to a syrup. Distilled water (50 mL) was added to the syrup and the mixture was stirred for 30 minutes at 4° C. Upon addition of chloroform (50 mL), the mixture was separated into layers, and the organic layer was extracted successively with water (50 mL each time, 5 times usually) until the pH of the water layer was approximately 5. The aqueous solutions so obtained were combined and extracted once with chloroform (50 mL); this chloroform solution and the chloroform solution from above were combined, dried over sodium sulfate, and evaporated to a syrup. Crystals, obtained by storing the syrup overnight at −20° C., were triturated with diethyl ether, and harvested by filtration.

Recrystallization from absolute ethanol yielded 2.0 g of the desired product. This compound was analyzed by mass spectrometry, infrared spectroscopy, NMR, liquid chromatography, and melting point, and proved to be the N-hydroxysuccinimide ester of acrylic acid.

EXAMPLE III

Preparation and Characterization of A Monomer/Polypeptide Conjugate

The N-hydroxysuccinimide ester of acrylic acid (NSA) was reacted with mouse monoclonal antibody (MAb) 2H1 (the corresponding hybridoma cell line has been deposited with the American Type Culture Collection and given ATCC# HB-8416) as follows: 2.2 mg MAb in 0.29M sodium carbonate buffer, pH 9.3, was added to 20 micrograms of NSA in a total volume of 0.5 mL. The reaction mixture was incubated at 37° C. for one hour with constant stirring. Of this solution, 100 microliters was then taken for an analysis by reversed-phase high-performance liquid chromatography (RP-HPLC), which revealed the amount of free acrylic acid (arising from nonspecific hydrolysis of NSA) and remaining NSA in the reaction mix (Table 1).

TABLE 1

| RESULTS OF HPLC ANALYSIS OF MONOMER CONJUGATION REACTION MIXTURE | | | |
|---|---|---|---|
| | Antibody | NSA (Activated monomer) | Monomer (Acrylic acid) |
| Amount added, nanomoles | 14.5 | 116.0 | 0.0 |
| Amount detected in solution, nanomoles | Not determined | 0.0 | 26.7 |

This indicated that a net of 89 nanomoles of monomer was attached to the 14.5 nanomoles of MAb for a ratio of 6.2 monomer molecules per MAb.

To remove residual NSA and its hydrolysis products and for further characterization of the derivatized antibody, 200 microliters of the reaction mixture was chromatographed on a column of Sephadex ® G-25 (beads of dextran cross-linked with epichlorohydrin from Pharmacia Fine Chemicals AB, Uppsala, Sweden) in the same carbonate buffer to which bovine serum albumin, 0.1 mg/mL, was added to prevent nonspecific adsorption of polypeptides to the Sephadex ® G-25.

To show that the purified monomer/antibody conjugate was still biologically active, it was tested in an enzyme-linked immunosorbent assay (ELISA), and the results indicated no loss of antigen binding capacity. For this purpose, the antigen (human IgG) was adsorbed to the surfaces of wells in a micro ELISA plate (96 wells). The wells were washed, residual nonspecific adsorbing sites on the plastic surface were blocked with bovine serum albumin, and then incubated with serial dilutions of the antibodies (control antibody and monomer/antibody conjugate). The plate was again washed, incubated with goat anti-mouse immunoglobulin conjugated to horseradish peroxidase (Tago, Inc., Burlingame, Calif. 94010), washed, and incubated with the substrates for horsradish peroxidase, o-phenylenediamine and hydrogen peroxide. Dilute aqueous sulfuric acid was added to stop the reaction, the plates were assayed on a micro ELISA reader, and the optical densities of each dilution of monomer/antibody conjugate compared with that of the control antibody. On a molar basis, the monomer/antibody conjugate demonstrated comparable activity to the nonconjugated antibody alone.

A sample of the monomer/antibody conjugate was then analyzed by isoelectric focusing. In this procedure, the polypeptide subunits of the proteins were separated according to their isoelectric point, or pH at which they had no net positive or negative charge. For this purpose, the heavy and light chains of the monomer/antibody conjugate were first dissociated in the presence of 3% (w/v) sodium dodecyl sulfate (SDS) and 5% (v/v) 2-mercaptoethanol and separated on the basis of molecular weight by electrophoresis in an SDS-polyacrylamide slab gel. The separated heavy and light chains were cut out from the gel and analyzed further by isoelectric focusing in a polyacrylamide slab gel according to their isoelectric point. Staining of the isoelectric focusing gel with dye (Coomassie Brilliant Blue R-250) provided a characteristic pattern of bands for each sample. Since both the heavy and light chains of antibodies are glycoproteins which contain intrinsic variations in their sialic acid content, each heavy and light chain can be separated by charge into a characteristic family of bands, with each band containing a polypeptide and differing amounts of sialic acid. As the reaction of the activated acrylic acid occurred primarily with amino functional groups on protein lysine residues, the addition of monomer to MAb would be expected to neutralize one positive charge on the protein subunit for each molecule of acrylic acid attached. This in turn would be expected to change the isoelectric point of the derivatized protein.

Figure 2:
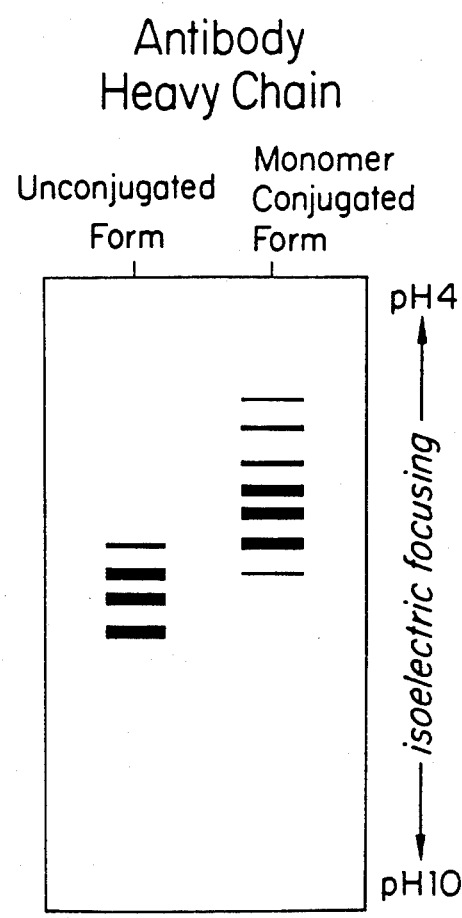
FIG. 2 is a diagrammatic representation of a polyacrylamide isoelectric focusing gel of the heavy chain of antibody 2H1 before and after conjugation with acrylic acid.
Figure 3:
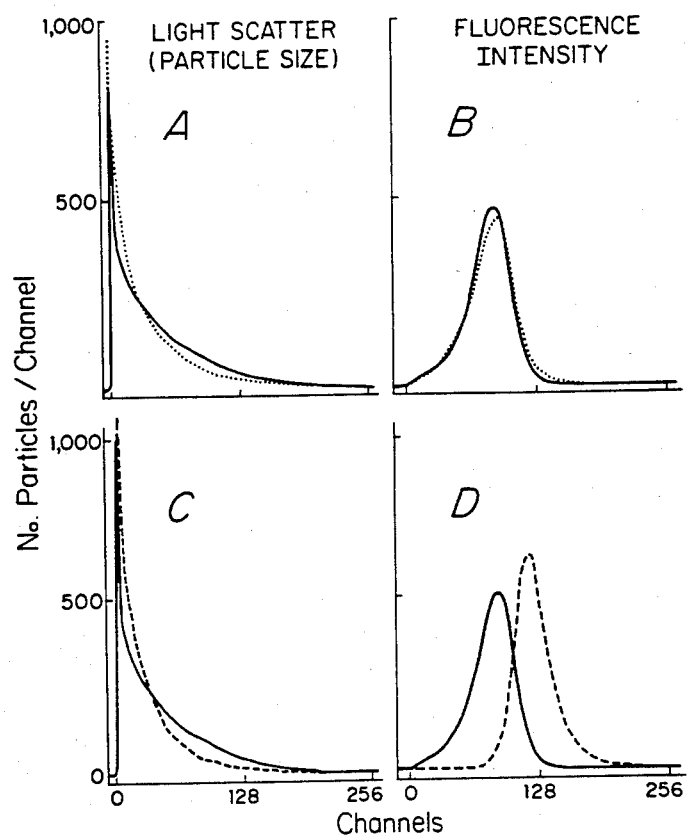
FIG. 3 depicts the incorporation of fluorescein-tagged monomer/polypeptide conjugates into insoluble polypeptide-containing polymer particles.

The results of the isoelectric focusing analysis indicated that each heavy chain was modified by the covalent attachment of approximately three acrylic monomers (FIG. 2). Analysis also indicated that the electrophoretic pattern of monomer-derivatized light chain was so close to the nonderivatized polypeptide pattern that essentially minimal conjugation of monomer to light chains had occurred. On this basis, it was estimated that six moles of acrylic acid monomer was conjugated to each mole of antibody (3 per heavy chain times 2 heavy chains per antibody), which was in agreement with the analysis by RP-HPLC.

EXAMPLE IV

Demonstration of Incorporation of Monomer/Polypeptide Conjugate into Polymer

In order to provide a means of identifying and monitoring the presence of polypeptides in polymers, the monomer/antibody conjugate (MAb-M) was covalently tagged with a fluorescent compound. For this compound, 88 micrograms (8.8 microliters of 10 mg/mL in DMSO) of fluorescein isothiocyanate isomer II (FITC) was added to 3.6 mg MAb-M in 1.2 mL of 0.29M carbonate buffer, pH 9.3. The mixture was stirred for 1 hour at 37° C. and chromatographed on a column of Sephadex ® G-25 in phosphate-buffered saline to which bovine serum albumin (0.01 mg/mL) had been added to prevent nonspecific adsorption to the column. This separated the fluorescein-tagged MAb-M from any free fluorescein isothiocyanate that remained in solution.

The fluorescein-tagged MAb-M conjugates were then copolymerized with additional HEMA to form insoluble polymer particles. Two methods were used to demonstrate the incorporation of the fluorescein-tagged MAb-M into the de novo synthesized polymer. Both methods, fluorescence microscopy and quantitative flow analysis with the fluorescence-activated cell sorter, actually measured the presence of fluorescence in the polymer particles. For comparison, two controls were used (samples a and b). In sample a, HEMA was polymerized by itself into insoluble polymer particles in a smaller version of the polymerization system of Example I (total volume: 1 ml). In sample b, 50 micrograms of a fluorescein-tagged (but not monomer-conjugated) "bystander" MAb was added to the polymerization system to test for nonspecific entrapment of bystander polypeptides during the formation of insoluble polymer particles. In neither case was any fluorescence seen to be associated with the polymer particles when viewed in the fluorescence microscope. In sample c, 50 micrograms of monomer-conjugated, fluorescein-tagged MAb-M was added to the polymerization system to test for specific incorporation of the polypeptide, via copolymerization, into the polymer particles. In this case, all of the fluorescence was seen to be associated with the polymer particles when viewed in the fluorescence microscope.

The same experiment was examined by quantitative flow analysis with a fluorescence-activated cell sorter. After the polymerization had proceeded for ten minutes, the suspension of polymer particles was diluted one-hundred-fold and then introduced into a flow cytometer (Becton Dickinson, FACS IV) equipped with an Argon ion laser light source. In this procedure, the suspended particles were carried single-file in a laminar stream of buffer. Interrogation of the particle stream with the laser beam generated light scatter each time a particle entered the laser pathway. The extent of the light scatter was a reflection of particle size and shape. Further, measurement of light scatter can also be used to electronically trigger a simultaneous measure of fluorescence emitted from the particle which was responsible for the light scatter signal. In this way, fluorescence specifically associated with polymer particles can be selectively measured.

The results can be summarized as follows: Light Scatter Analysis. Light scatter analysis (panels A and C) of polymer particles formed from HEMA alone (solid line), polymer particles formed from HEMA polymerized in the presence of bystander antibody (dotted line), and polymer particles formed by copolymerization of HEMA with fluorescein-tagged MAb (dashed line), shows that the particle size distribution was substantially the same for all three samples. Fluorescence Analysis. Panel B compares the fluorescence intensity of polymer particles formed from HEMA alone (solid line) and polymer particles formed from HEMA polymerized in the presence of bystander antibody (dotted line). The fluorescence intensity was substantially the same for both samples. Since the intensity was substantially the same regardless of whether or not fluorescein-tagged bystander antibody was present, the weak fluorescence signal of both samples was assumed to be due to autofluorescence of the HEMA polymer itself and indicated that there was minimal nonspecific entrapment of the bystander antibody in the polymer. Panel D compares the fluorescence intensity of polymer particles formed from HEMA alone (solid line) and those formed by copolymerization of HEMA with the monomerderivatized, fluorescein-tagged MAb (dashed line).

The fluorescence intensity of the copolymer particles (monomer-derivatized, fluorescein-tagged MAb and HEMA) was shifted over 28 channels. The fluorescence intensity scale (x axis) is logarithmic, and a shift of 28 channels corresponded to a three-fold increase in fluorescence intensity. This dramatic increase in the fluorescence intensity provided conclusive evidence that the monomer-derivatized, fluorescein-tagged MAb was integrally incorporated into the polymer particles.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method of selectively removing substances from a solution or mixture, comprising:

covalently bonding a polymerizable organic monomer to a polypeptide that has binding activity to the substance to form a monomer/polypeptide conjugate;

contacting the substance with the monomer/polypeptide conjugate; and polymerizing the monomer/polypeptide conjugate to form an insoluble polymer which can be separated from the solution.

2. The method of claim 1 wherein the substance to be removed is an antigen, the polypeptide is an antibody, and the solution or mixture is aqueous.

3. The method of claim 1 wherein the monomer/polypeptide conjugate is homopolymerized.

4. The method of claim 1 wherein the monomer/polypeptide conjugate is copolymerized with additional nonderivatized organic monomers.

5. The method of claim 4 wherein the nonderivatized monomer is one selected from the group consisting of at least one ethylenically and/or acetylenically unsaturated monomer and/or multifunctional cross-linking compound.

* * * * *